United States Patent [19]

Hill et al.

[11] Patent Number: 5,538,667
[45] Date of Patent: Jul. 23, 1996

[54] ULTRAMULSIONS

[75] Inventors: Ira D. Hill, Locust, N.J.; Dale G. Brown, Stafford, Tex.

[73] Assignee: WhiteHill Oral Technologies, Inc., Hazlet, N.J.

[21] Appl. No.: 144,778

[22] Filed: Oct. 28, 1993

[51] Int. Cl.$^6$ .............. B01J 13/00; C11D 1/722; C11D 1/82
[52] U.S. Cl. .......... 252/312; 106/287.14; 252/308; 252/314; 510/417; 510/421; 510/466
[58] Field of Search ............... 252/308, 312, 252/314, 174.15; 106/287.14

[56] References Cited

U.S. PATENT DOCUMENTS

| | | | |
|---|---|---|---|
| 2,702,276 | 2/1955 | Green | 252/8.6 |
| 3,748,275 | 7/1973 | Bernheim et al. | 252/312 |
| 3,962,119 | 6/1976 | Cosentino et al. | 252/312 X |
| 4,039,469 | 8/1977 | Raleigh | 252/314 X |
| 4,400,288 | 8/1983 | Dhanani et al. | 252/174.15 X |
| 4,780,245 | 10/1988 | Burke et al. | 252/312 |
| 4,814,376 | 3/1989 | Tanaka et al. | 252/314 X |
| 5,071,573 | 12/1991 | Coffindaffer et al. | 252/312 X |

OTHER PUBLICATIONS

Prince, C. M., Microemulsion Theory & Practices, pp. 1, 2, 3, 33, 34 and 35, Academic Press Inc., New York, NY (1977).

Technical Literature re Dow Corning 360 Medical Fluids, Dow Corning Corporation (1989).
Technical Literature re Pluronic & Tetronic Block Copolymer Surfactants, Dow Corning Corporation (ca. 1980).
Technical Literature re Biological Safety Evaluation of Dow Corning 360 Medical Fluid, Dow Corning Corporation (ca. 1980).
Rowe et al., The Journal of Industrial Hygiene & Toxicology, vol. 30, No. 6, pp. 332-352 (1948).

Primary Examiner—Richard D. Lovering
Attorney, Agent, or Firm—Ernest V. Linek

[57] ABSTRACT

The present invention relates to water-free, co-solvent free, stable, dispersions of certain polydimethylsiloxanes in certain nonionic, poloxamer surfactants; wherein:

a. the dispersed polydimethylsiloxanes, which are insoluble in said surfactant, are oriented by the surfactant such that when dispersed in water they are particularly adept at forming oriented, monolayer coatings on various substrates, and b. the particle size of the dispersed polydimethylsiloxane is from between about 0.5 and about 10 microns, with a particle size distribution such that from between about 80 and 95% of the dispersed polydimethylsiloxane is within this particle size range. These stable dispersions are described as ultramulsions, which, together with their physical properties, distinguishes them from emulsions, microemulsions and solutions.

19 Claims, 3 Drawing Sheets

ULTRAMULSIONS

BACKGROUND OF THE INVENTION

The present invention relates to unique compositions comprising a dispersion of certain polydimethylsiloxanes in certain nonionic poloxamer surfactants. When added to water these dispersions are stable and are distinct from solutions, emulsions and microemulsions. These dispersions are referred to hereinafter as ultramulsions. These ultramulsions offer excellent utility in a broad range of coating applications, which are described in detail below.

The uniqueness and novelty of the ultramulsions of the invention are more readily appreciated when these compositions are compared to other dispersions such as emulsions and microemulsions.

When a system consists of a single liquid phase it is described as a solution. A system containing two or more liquid phases is described as a multiphase solution or emulsion.

According to Becher, an emulsion is an unstable heterogeneous system in which the diameters of the dispersed droplets in general exceed 1000 A. Becher P. in "*Emulsions, Theory & Practice*", (P. Becher, Ed.) page 2, Rheinhold, N.Y., 1965.

A more comprehensive definition of emulsion is advanced by Clayton: "An emulsion is a system containing two liquid phases, one of which is dispersed as globules in the other. The liquid which is broken up into globules is termed the dispersed or discontinuous phase, while the liquid surrounding the globules is known as the continuous phase or dispersing medium" Clayton, W., *The Theory of Emulsions and Their Technical Treatment*, 4th Ed. page 1, the Blakiston Co., Philadelphia, 1943. It is well accepted that, mechanical work is required to effect such an emulsion, see Bancroft W. D., *J. Phy. Chem.*, 17: 501, (1913).

According to Prince, an emulsion may be defined as a dispersion of two (or more) mutually insoluble liquids, one in the other. Because of the surface tension forces at play between the two liquids, the dispersed phase consists of spherical droplets. Prince, L. M. *Microemulsion Theory & Practice*, pg. 2, Academic Press Inc., New York, N.Y. (1977). See also Prince, L. M. in *Biological Horizons in Surface Science*, pg. 361, Academic 1973, Emulsions, are generally not stable and upon standing or after centrifuging tend to separate into two or more liquid layers.

The three definitions of emulsions set forth above share one common attribute, that is, mechanical work must be put into the emulsions described in order to disperse one liquid in the other in the form of droplets. This mechanical work can be in the form of agitation, homogenization, ultrasonication, etc.

In contrast, dispersions of very small droplet sizes which are formed spontaneously without the input of any mechanical work are called microemulsions. See Prince 1977, p. 3. Generally, two surfactants are used in forming microemulsions, i.e. a water soluble surfactant and a co-surfactant such as alcohol, where one phase of the microemulsion is generally water. Thus, dilution or adulteration of the dispersed phase by the co-solvent generally accompanies microemulsion formation. The ratio of surfactant to dispersed phase in microemulsions is much higher than that of emulsions. Microemulsions are further characterized as optically clear or opalescent and when spun in a laboratory centrifuge for 5 minutes at 100 G's, the dispersion remains stable and does not separate.

Thus, fine particle sizes, exceptional stability and rheological properties that can be easily adjusted, distinguish microemulsions from emulsions. Moreover, to late, no microemulsions have appeared in which one of the mutually insoluble liquids is not water. See Prince, page 34, (1977).

SUMMARY OF THE INVENTION

The ultramulsions of the present invention combine certain characteristics of emulsions with certain features of microemulsions. That is, like emulsions, they are two phase systems comprising a polydimethylsiloxane dispersed in a continuous, nonionic, surfactant phase, wherein the polydimethylsiloxane is insoluble in the surfactant. Unlike emulsions, but like microemulsions, these dispersions are stable. Unlike microemulsions, but like emulsions, mechanical work is required to form the ultramulsions. Like microemulsions, but unlike emulsions, these ultramulsions are not formed spontaneously. Like emulsions, the ultramulsions do not contain a cosolvent commonly found in microemulsions. Of course, the ultramulsions of the present invention can be dispersed in various liquids such as water as stable dispersions. The dispersions of ultramulsions in water have excellent utility in various aqueous based coatings etc. See Tables 1 and 2.

While not wishing to be bound by theory, it is hypothesized that unlike either emulsions or microemulsions, the dispersed polydimethylsiloxanes of the ultramulsions of the present invention are oriented with their polar moieties in one general plane and their hydrophilic moieties in a plane approximately opposite that of the polar moieties. This orientation promotes bonding between the polar or hydrophilic moieties and various substrates thereby effecting oriented, monolayer coatings of the polydimethylsiloxane onto various substrates. These oriented dispersions of polydimethylsiloxanes have a broad range of utility as detailed below in Tables 1 and 2.

For purposes of the present invention:

a. polydimethylsiloxane means a clear, colorless liquid such as Dow Corning® 360 medical fluid; a water-dilutable, nonionic emulsion containing 30% by weight Dow Corning® medical Antifoam A compound (Simethicone USP); Dow Corning® 1500 Silicone Antifoam which is an opaque grey to white, pourable liquid containing silica filled polydimethylsiloxanes, Dow Corning® 200 fluids, 60,000 to 100,000 centistrokes (cs) which are high viscosity polydimethylsiloxane polymers manufactured to yield linear polymers with average kinematic viscosities between about 60,000 to 100,000 cs. Preferred polydimethylsiloxanes suitable for the present invention are described in various product brochures published by Dow Corning Corporation, Midland, Mich. under product designations such as Dow Corning®, 360 Medical Fluid, Dow Corning® 200 Fluids, etc. See Tables 1 and 2 below.

b. nonionic poloxamer surfactant means block copolymers of ethylene oxide and propylene oxide ranging from flowable liquids of varying viscosities, to paste, prills and cast solids with molecular weights from 1,100 to 150,000. Suitable nonionic surfactants are manufactured and marketed by BASF Corporation under the trademarks Pluronic®. Particularly preferred nonionic surfactants are Pluronic F-68, F-88, F-108 and Pluronic F-127. These are described in a BASF brochure entitled "Pluronic® and Tetronic Block Copolymer Surfactant." These nonionic surfactants suitable for the present invention can be described by the following structure.

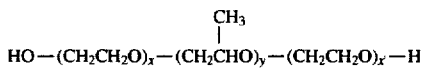

where x, y and x' are whole numbers. Surprisingly, the nonionic surfactants of choice for the ultramulsions of the present invention are reported in the referenced brochure to have marginal detergency, emulsification and wetting properties. See Tables 1 and 2.

c. stable is defined as, a dispersion of the ultramulsion in water when subjected to centrifuging in a 100° C. environment for 5 minutes, less than about 10% by weight of the ultramulsion separates from the continuous water phase. See Table 2.

d. water-free means, that the ultramulsion of polydimethylsiloxane and nonionic surfactant is substantially free from water.

e. solvent free means, that the ultramulsion of polydimethylsiloxane and nonionic surfactant is substantially free from co-solvents such as ethanol, isopropanol, etc.

f. oriented means, that the polar moieties of the "uncoiled" polydimethylsiloxane in the ultramulsion are generally aligned in one plane with the hydrophilic oil seeking moieties aligned in a second plane generally 180° from the polar moieties such as illustrated in FIG. 2.

g. monolayer means, that a monomolecular film of the ultramulsion of the invention when dispersed in water is attracted to a substrate by secondary bonding force to form a coating thereon.

DETAILED DESCRIPTION OF THE PREFERRED EMBODIMENTS

Figure 1:
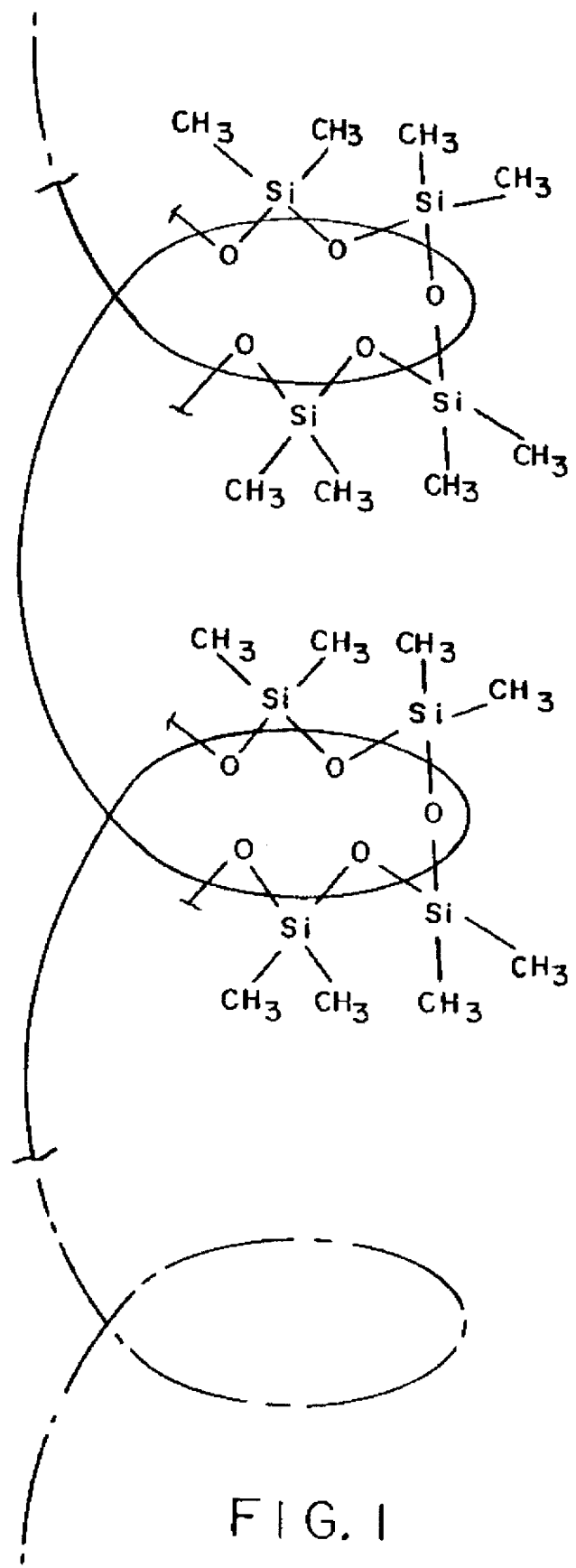
FIG. 1 illustrates the "coiled" molecular configuration of polydimethylsiloxanes.

Referring to the drawings, FIG. 1 illustrates the accepted "coiled" configuration advanced for polydimethylsiloxanes, wherein the methyl moieties are oriented outward while the oxygen moieties are oriented inward towards the axis of the coil or helix. This configuration does not readily promote "bonding" between the oxygen moieties and compatible surfaces.

Figure 2:
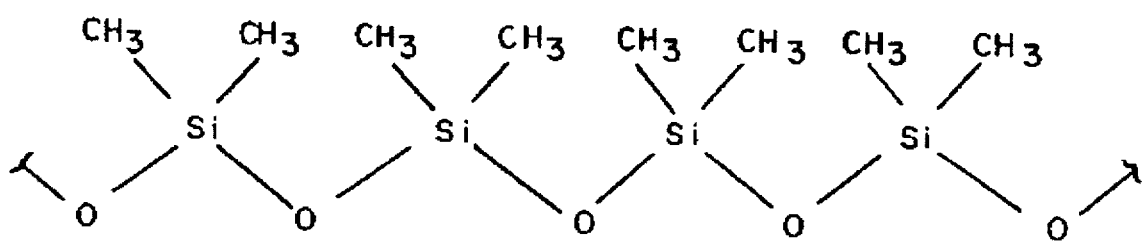
FIG. 2 illustrates the molecular configuration of oriented polydimethylsiloxanes after ultramulsion processing.

FIG. 2 illustrates the "uncoiled oriented" configuration proposed for polydimethylsiloxanes that have been dispersed in the stable, ultramulsions of the present invention, wherein the oxygen moieties are generally oriented in one plane distinct from that of the methyl moieties. This proposed uncoiled oriented configuration appears to support the unique and unexpected "bonding" properties of the ultramulsions of the present invention, as evidenced by the various coating applications of these ultramulsions. See Tables 1 and 2.

Figure 3:
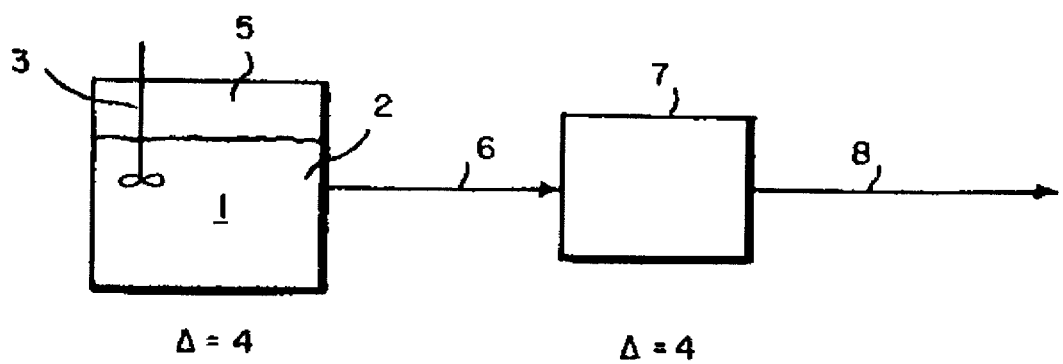
FIG. 3 illustrates schematically an ultramulsion process of the invention.

FIG. 3 illustrates the ultramulsion process of the present invention wherein a nonionic surfactant and a polydimethylsiloxane 1, substantially free from water and co-solvent, are mixed in vessel 2, provided with mixing means 3, heat source 4, and inert head space 5. The heated and mixed surfactant/polydimethylsiloxane 6, is then subjected to high shear dispersion at an elevated temperature in dispersing means 7, to produce the ultramulsion 8, of the invention.

Figure 4:
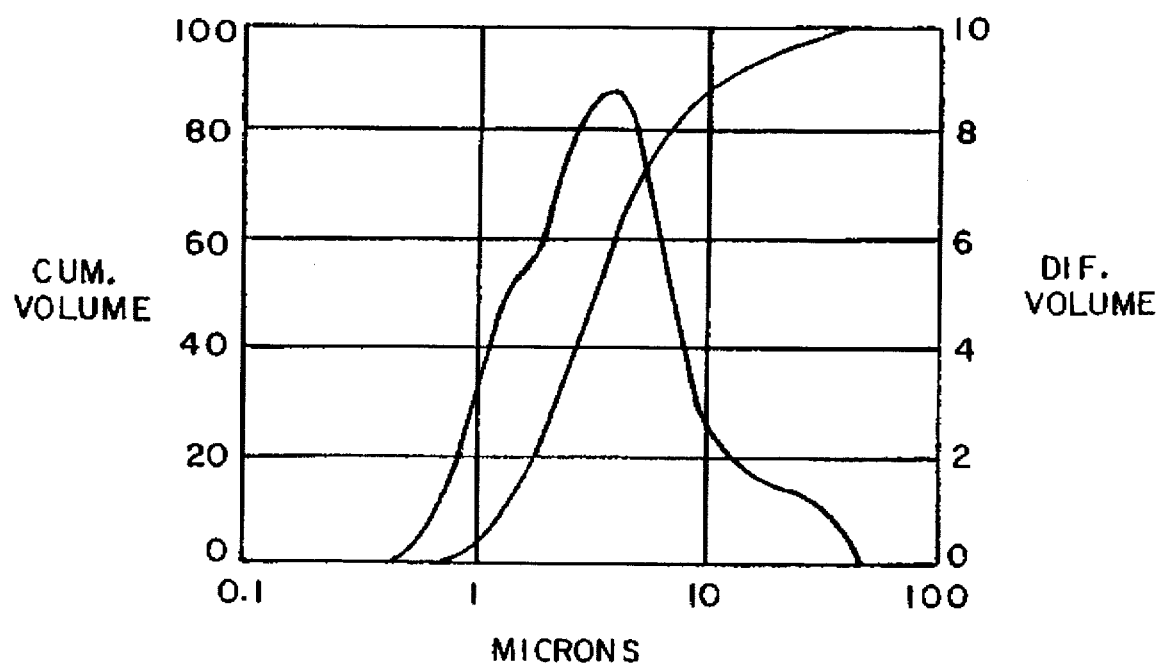
FIGS. 4 and 5 illustrate that the ultramulsions of the invention produced via various high shear dispersions have particle size distribution of 80+% under 10 microns.

FIG. 4 is a chart describing the particle size distribution of an ultramulsion of the invention containing: 50% by weight nonionic surfactant and 50% by weight polydimethylsiloxane (12,500 cs) produced in a continuous process with an IKA Work dispersing means, (high shear dispersing) with an inlet temperature of 140° C. and an outlet temperature of 210° C.

Figure 5:
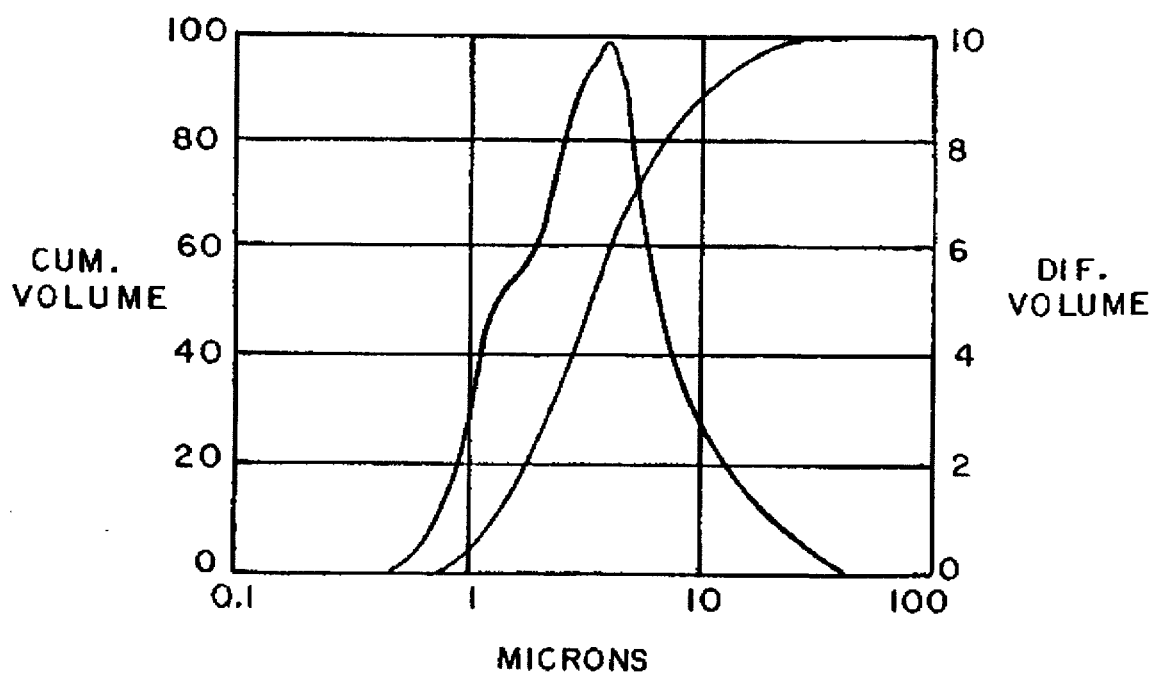

FIG. 5 is a chart describing the particle size distribution of an ultramulsion of the invention containing 50% by weight nonionic surfactant and 50% by weight polydimethylsiloxane (12,500 cs) produced in a batch process with a Ross M/E 100 LC dispersing means fitted with a 20 mesh screen, operated at a temperature from 120° to 160° C.

Emulsions of various coating substances including polydimethylsiloxanes in various surfactants including nonionic surfactants are disclosed and claimed in U.S. Pat. Nos. 4,911,927; 4,942,034; 4,950,479; 5,009,881; 5,032,387; 5,057,306; 5,057,307; 5,057,308; 5,057,309; ,057,310; 5,098,711 and 5,165,913. There is no teaching in these references that these emulsions are stable nor that the "coating" substances are oriented as they are in the ultramulsions of the present invention.

The ultramulsions of the present invention have utility in a broad range of coating applications such as: anti-gas/antacid products, plaque control agents, medical lubricants, mold release agents, plasticizers, antifoam agents, polishes, paints, cutting oils, cleaners, emollients, drug delivery vehicles, anesthetic enhancers, blood additives, etc. These are detailed in Table 1 and 2 below.

The safety of polydimethylsiloxanes for use in these various products is well documented. See Rowe et al., *Journal of Industrial Hygiene*, Vol. 30, No. 6, 332–352, November 1948. See also Calandra et al., *ACS Polymer Preprints*, 17, 1–4 (1976) and Kennedy et al., *J. Toxicol. & Environmental Health*, 1, 909–920 (1976).

As noted above, the polydimethylsiloxanes useful in the compositions of the present invention are described as polymethylsiloxanes with the chemical composition $(CH_3)_3SiO[SiO(CH_3)_2]_nSi(CH_3)_3$, wherein n is a whole number, preferably ranges from between about 10 and about 400.

These polydimethylsiloxanes have viscosities ranging from between about 100 and about 100,000 cs. and are generally described as having molecular weights between about 800 and about 30,000.

As noted above, the preferred nonionic poloxamer surfactants useful in the coating compositions of the present invention are described as polyoxyethylene-polyoxypropylene block copolymers such as Pluronic F-68, F-88, F-108 and F-127 (BASF) which have molecular weights of at least about 1000 such as described in U.S. Pat. Nos. 4,343,785; 4,465,663; 4,511,563 and 4,476,107.

These surfactants range from solids to liquids at room temperature and are generally described as having molecular weights between about 1,100 and 150,000.

The ratio of surfactant to polydimethylsiloxane in the ultramulsion coating compositions of the present invention can range from between about 400:1 and about 1:2. In a preferred embodiment of the invention the ratio of surfactant to polydimethylsiloxane is from between about 25:1 and 1:2. See Tables 1 and 2.

Some of the ultramulsions of the present invention are solid at room temperature. At elevated temperature the viscosity of these ultramulsions can range from between about 8,000 and about 40,000 cs at 130° C. In a preferred embodiment of the invention the viscosity of these ultramulsions at 130° C. can range from between about 10,000 and about 25,000 cs. See also Table 1.

The particle size of the polydimethylsiloxane in the ultramulsions of the present invention can range from between about 0.5 and about 10 microns. In a preferred embodiment of the present invention the particle size of the polydimethylsiloxane in the ultramulsion ranges from between about 1 and about 5 microns. The particle size distribution of the polydimethylsiloxane in the ultramulsions of the present invention generally range from between about 80 and about 95% of the particles under 10 microns. See FIGS. 4 and 5. In a preferred embodiment of the present invention, from between about 80 and about 95% of the particles are under 5 microns. See also Table 2.

The ultramulsions of the invention are prepared as follows:

Generally, the nonionic surfactant is heated to a temperature at which it becomes a liquid. The polydimethylsiloxane is dispersed in the heated surfactant with various high shear dispersing means.

Specifically the molten surfactant is mechanically stirred along with the silicone fluid. This mixture is subjected to high-shear dispersions with a means such as the IKA-WORKS DISPAX-Reactor with at least one superfine generator, alternatively, a Ross Model M.E, 100 LC fitted with a 20 mesh screen or a ultrasonicator such as MEDSONIC XL2010 fitted with 800-C Flow Cell & 800-21CT ¾ inch flanged horn can be used.

Various ultramulsions which were prepared and analyzed are described in detail in the examples below.

EXAMPLE 1

Dow Corning® Medical Antiform AF Emulsion, comprised of 30% simethicone, 14% stearate emulsifier, 6.075% sorbic acid and approximately 56% water was dispersed in water at 0.5% and 0.16% and centrifuged for 15 minutes at 3450 RPM (International Clinical Centrifuge Model CL). The polydimethylsiloxane completely separates some to the top 1/10 of the tube (the silica containing portion), some to the bottom 1/10 (polydimethylsiloxane only), leaving the intervening water layer completely free of polydimethylsiloxane.

Examples 2 through 20 are set forth in Table 1 below, while Examples 21 through 32 are set forth in Table 2 below.

TABLE 1

| Example | Nonoinic Surfactant Type | % | Polydimethylsiloxane Type | Viscosity (cs) | % | Utility (5) |
|---|---|---|---|---|---|---|
| 2 | F-108 | 90 | DC 360 Med. Fluid | 1,000 | 10 | (A), (B), (C), (L), (M), (N) |
| 3 | F-127 | 80 | DC 200 Fluid | 350 | 20 | (H), (J), (M), (N) |
| 4 | F-108 | 98 | DC 360 Medical Fluid | 12,500 | 2 | Transparent (A) |
| 5 | F-108 | 60 | DC 200 Fluid | 100 | 40 | (H), (M), (J), (N) |
| 6 | F-127<br>F-108 | 25<br>25 | DC 360 Medical Fluid | 100,000 | 50 | (B), (C), (E), (N), (F), (G) |
| 7 | F-127 | 50 | DC 200 Fluid | 10,000 | 50 | (H), (J), (K), (M), (N) |
| 8 | F-127 | 33 | DC Medical Fluid | 12,500 | 66 | (B), (C), (D), (E), (F), (G), (I), (K), (L), (N) |
| 9 | F-127<br>F-108 | 95 | DC 200 Fluid | 1,000 | 5 | (M), (N) |
| 10 | F-127 | 33 | DC 200 Fluid | 100 | 66 | (H), (J), (M), (N) |
| 11 | F-108<br>F-127 | 40<br>40 | DC 360 Medical Fluid<br>DC 360 Medical Fluid | 1,000<br>12,500 | 10<br>10 | (B), (C), (D), (F), (G), (K), (N) |
| 12 | F-108 | 60 | DC 200 Fluid | 350 | 40 | (H), (J), (M), (N) |
| 13 | F-108 | 50 | DC Medical Fluid | 1,000 | 50 | (I), (J), (L), (N), (F), (G) |
| 14 | F-127 | 33 | DC 360 Medical Fluid | 350 | 66 | (I), (J), (L), (N) |
| 15 | F-108 | 95 | DC 200 Fluid | 100 | 5 | (M) |
| 16 | F-127 | 40 | DC 200 Fluid | 1,000 | 60 | (M), (N), (K), (J), (H) |
| 17 | F-68 | 90 | DC 200 Fluid | 1,000 | 10 | (J), (K), (M), (N) |
| 18 | F-88 | 50 | DC 200 Fluid | 100,000 | 50 | (H), (J), (K), (N) |
| 19 | F-88 | 80 | DC 200 Fluid | 350 | 20 | (J), (K), (M), (N) |
| 20 | F-68 | 33 | DC 200 Fluid | 100 | 66 | (H), (J), (K), (M), (N) |

\* See Footnote 5 in Table 2

TABLE 2

| Example | Pluronic® F-108 Noionic Surfactant (1) (% by wt.) | Dow Corning® 360 Medical Fluid Polydimethyl/ siloxane (2) (% by wt.) | Work Force to prepare Ultramulsion Means | Temp°C. | Particle size Distribution in % (3) 1–3 μ | 4–9 μ | >10 μ | Stability (4) | Utility of Ultramulsion (5) |
|---|---|---|---|---|---|---|---|---|---|
| 21 | 90 | 10 | Lightening mixer | 160 | 0 | 40 | 60 | easily separates, very unstable | Not ultramulsion |
| 22 | 66 | 33 | Lightening mixer | 160 | 0 | 45 | 55 | easily separates, very unstable | Not ultramulsion |
| 23 | 90 | 10 | Greerco Homogenizer | 120 | 10 | 25 | 65 | More than 10% separates on centrifuging, moderately unstable | Not ultramulsion |
| 24 | 66 | 33 | Greerco Homogenizer | 120 | 10 | 30 | 60 | More than 10% separates on centrifuging, moderately unstable | Not ultramulsion |
| 25 | 90 | 10 | Ross with open screen | 120 | 30 | 30 | 40 | More than 10% separates on centrifuging, moderately unstable | Not ultramulsion |
| 26 | 66 | 33 | Ross with open screen | 160 | 30 | 40 | 30 | More than 10% separates on centrifuging, moderately unstable | Not ultramulsion |
| 27 | 90 | 10 | Ross with 20 mesh screen | 100 to 120 | 90 | 10 | 0 | no separation on centrifuging, good stability | Good utility for A, B, C, L, M, N |
| 28 | 66 | 33 | Ross with 20 mesh screen | 100 to 160 | 90 | 10 | 0 | no seperation on centrifuging, good stability | Good utility for B, C, D, E, F, G, K, L, N |
| 29 | 80 | 20 | IKA | 100 to 150 | 50 | 40 | 10 | no separation on centrifuging, good stability | Good utility for B, E, J, L, M, N |
| 30 | 50 | 50 | IKA | 140 to 210 | 43 | 44 | 13 | no separation on centrifuging, good stability | Good utility for B, C, D, E, F, G, H, I, J, K, L, N |
| 31 | 50 | 50 | Ross with 20 mesh screen | 140 to 160 | 40 | 50 | 10 | no separation on centrifuging, good stability | Good utility for B, C, D, E, F, G, H, I, J, K, L, N |
| 32 | 95 | 5 | ultrasonic | 140 to 260 | 60 | 40 | 0 | no separation on centrifuging, good stability | Transparent A |

(1) other nonionic surfactants such as Pluronic F-68, F-88, F-127 and L-31 can also be used to prepare comparable ultramulsions.
(2) other polydimethylsiloxanes such as Dow Corning® 1500 Silicone Antiform and Dow Corning® 200 Fluids can also be used to prepare comparable ultramulsions.
(3) In Examples 21–29 and 32, particle size distribution determined via phase contrast microscopic examination. Examples 30 and 31 were analyzed via MICROTEC full range particle analyzer.
(4) Stability is demonstrated in water dispersion at 0.5% by weight ultramulsion or 0.167% ultramulsion followed by centrifugation at full speed in a laboratory centrifuge (International Clinical Centrifuge Model CL) at 3450 RPM for one hour, where: (a) very unstable means top ⅓ of tube contains approximately 80% of the polydimethylsiloxane suspension and lower ⅓ of tube is transparent indicating general absence of polydimethylsiloxane; (b) moderately unstable means top ⅓ of tube contains up to 30% of polydimethylsiloxane and lower ⅓ of tube is transparent; and (c) good stability means, top 1/20 of tube contains barely visible excess of polydimethylsiloxane, with remainder of the tube uniform in appearance.
(5) A = utility in alcohol free aqueous base mouthrinse
B = utility in toothpaste
C = utility in dental floss
D = utility in confectionery (sugar plating)
E = utility in chewing gum coating
F = utility in antacid tablet
G = utility in antacid liquid TABLE 2-continued

| | Pluronic® F-108 Noionic Surfactant (1) | Dow Corning® 360 Medical Fluid Polydimethyl/ siloxane (2) | Work Force to prepare Ultramulsion | | Particle size Distribution in % (3) | | | | Utility of |
|---|---|---|---|---|---|---|---|---|---|
| Example | (% by wt.) | (% by wt.) | Means | Temp°C. | 1–3 μ | 4–9 μ | >10 μ | Stability (4) | Ultramulsion (5) |

H = utility in non volatile mold release
I = utility in lubricant for medical instruments
J = utility in plasticizer
K = utility in antiform
L = utility in drug delivery vehicle
M = utility in cleaners
N = utility in cosmetic and skin care products.

What is claimed is:

1. Water-free, co-solvent free, ultramulsions comprising nonionic poloxamer surfactant and polydimethylsiloxane insoluble in said nonionic poloxamer surfactant wherein:

a. said polydimethylsiloxane has the chemical composition $(CH_3)_3SiO[SiO(CH_3)_2]_nSi(CH_3)_3$, wherein n is a whole number from between about 10 and about 400;

b. said nonionic poloxamer surfactant has the chemical composition

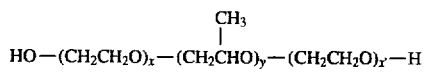

wherein x, y, and x' are whole numbers;

c. the viscosity of the polydimethylsiloxane ranges from between about 100 and about 100,000 cs;

d. the particle size of most of the polydimethylsiloxane in the ultramulsion is from between about 0.5 and about 10 microns;

e. from between about 80% and 95% of said polydimethylsiloxane particles in the ultramulsions are from between about 1 and about 10 microns;

f. the nonionic poloxamer surfactant is a polyoxyethylene-polyoxypropylene block copolymer having a molecular weight from between about 1,100 and about 150,000;

g. the ratio of nonionic poloxamer surfactant to polydimethylsiloxane is from between about 400:1 and about 1:2; and h. the viscosity of the ultramulsion is from between about 8,000 and about 40,000 cs at 130° C., and i. the ultramulsion dispersed in water is stable.

2. An ultramulsion according to claim 1, wherein the ratio of said nonionic poloxamer surfactant to said polydimethylsiloxane is 9:1 and 90% of the polydimethylsiloxane particles are from between about 1 and 3 microns.

3. An ultramulsion according to claim 1, wherein the ratio of said nonionic poloxamer surfactant to said polydimethylsiloxane is 2:1 and 100% of the polydimethylsiloxane dispersion is less than 10 microns.

4. An ultramulsion according to claim 1, wherein the ratio of said nonionic poloxamer surfactant to said polydimethylsiloxane is 1:1 and the polydimethylsiloxane particles in said ultramulsion are less than 10 microns.

5. An ultramulsion according to claim 1, wherein the polydimethylsiloxane is uncoiled and oriented wherein the oxygen moieties are generally oriented in a plane distinct from that of the methyl/moieties.

6. An ultramulsion according to claim 1, wherein the nonionic poloxamer surfactant is selected from the group consisting of, flowable liquids of varying viscosities, pastes, prills and cast solids.

7. An ultramulsion according to claim 1, wherein the ratio of nonionic poloxamer surfactant to polydimethylsiloxane is 1:1 and at least 80% of the polydimethylsiloxane dispersed particles are between 1 and 9 microns.

8. An ultramulsion according to claim 1, wherein the ratio of nonionic poloxamer surfactant to polydimethylsiloxane is 9:1 and about 90% of the polydimethylsiloxane dispersed particles are between 1 and 3 microns.

9. An ultramulsion according to claim 1, wherein the ratio of nonionic poloxamer surfactant to polydimethylsiloxane is 2:1 and about 90% of the polydimethylsiloxane dispersed particles are between 1 and 3 microns.

10. An ultramulsion according to claim 1, wherein the ratio of nonionic poloxamer surfactant to polydimethylsiloxane is 4:1 and about 90% of the polydimethylsiloxane dispersed particles are between 1 and 9 microns.

11. An ultramulsion according to claim 1, wherein the ratio of nonionic poloxamer surfactant to polydimethylsiloxane is 9.5:0.5 and about 100% of the polydimethylsiloxane dispersed particles are between 1 and 9 microns.

12. An ultramulsion according to claim 1, wherein the polydimethylsiloxane has a viscosity of 12,500 cs and the nonionic poloxamer surfactant is a solid at room temperature.

13. A method of manufacturing ultramulsions as described in claim 1 comprising, heating said nonionic poloxamer surfactant and polydimethylsiloxane mixture in a heated, stirred vessel substantially free from water, followed by subjecting said mixture to high shear dispersion with high shear dispersing means.

14. A method according to claim 13, wherein the heated vessel is provided with an inert head of gas.

15. A method according to claim 13, wherein said high shear dispersing means is fitted with a small orifice.

16. A method according to claim 13 wherein said high shear dispersing means is an ultrasonication means.

17. A method according to claim 13, wherein the high shear dispersion is achieved with dispersing means selected from the group consisting of an IKA-WORKS DISPAX REACTOR fitted with at least one superfine generator, a ROSS MODEL M.E. 100 2C fitted with a 20 mesh screen, and a ultrasonic MEDSONIC XL2010 fitted with 800-C flow cell and 800 21CT ¾ inch flanged horn.

18. A stable aqueous dispersion comprising water and dispersed therein an ultramulsion comprising a nonionic poloxamer surfactant and a polydimethylsiloxane insoluble in said nonionic poloxamer surfactant wherein:

a. said polydimethylsiloxane has the chemical composition $(CH_3)_3SiO[SiO(CH_3)_2]_nSi(CH_3)_3$, wherein n is a whole number from between about 10 and about 400;

b. said nonionic poloxamer surfactant has the chemical composition

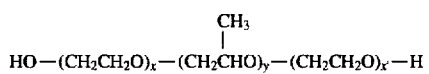

wherein x, y, and x' are whole numbers;
c. the viscosity of the polydimethylsiloxane ranges from between about 100 and about 100,000 cs;
d. the particle size of most of the polydimethylsiloxane in the ultramulsion is from between about 0.5 and about 10 microns;
e. from between about 80% and 95% of said polydimethylsiloxane particles in the ultramulsions are from between about 1 and about 10 microns;
f. the nonionic poloxamer surfactant is a polyoxyethylene-polyoxypropylene block copolymer having a molecular weight from between about 1,100 and about 150,000;
g. the ratio of nonionic poloxamer surfactant to polydimethylsiloxane is from between about 400:1 and about 1:2; and
h. the viscosity of the ultramulsion is from between about 8,000 and about 40,000 cs at 130° C., and
i. the ultramulsion dispersed in water is stable.

19. A stable aqueous dispersion according to claim 18, wherein the dispersed polydimethylsiloxane forms monolayer films suitable for secondary bonding on receptive substrates.

* * * * *